(12) United States Patent
Kaller et al.

(10) Patent No.: US 10,106,486 B2
(45) Date of Patent: Oct. 23, 2018

(54) METHOD FOR PRODUCING CARBOXYLIC ACID ESTERS AND THE USE THEREOF AS PLASTICIZERS

(71) Applicant: BASF SE, Ludwigshafen (DE)

(72) Inventors: Martin Kaller, Mannheim (DE); Michael Koch, Speyer (DE); Boris Breitscheidel, Waldsee (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/033,296

(22) PCT Filed: Oct. 30, 2014

(86) PCT No.: PCT/EP2014/073272
§ 371 (c)(1),
(2) Date: Apr. 29, 2016

(87) PCT Pub. No.: WO2015/063189
PCT Pub. Date: May 7, 2015

(65) Prior Publication Data
US 2016/0264509 A1 Sep. 15, 2016

(30) Foreign Application Priority Data

Oct. 31, 2013 (EP) ..................................... 13191071
Aug. 11, 2014 (EP) ..................................... 14180491

(51) Int. Cl.
*C07C 67/08* (2006.01)
*C08K 5/12* (2006.01)
*C08K 5/00* (2006.01)

(52) U.S. Cl.
CPC ................ *C07C 67/08* (2013.01); *C08K 5/12* (2013.01); *C08K 5/0016* (2013.01)

(58) Field of Classification Search
CPC ......... C07C 67/08; C07C 69/80; C07C 69/82; C07C 67/48; C07C 69/76; C07C 67/12; C08K 5/12; C08K 5/0016; Y02P 20/582
See application file for complete search history.

(56) References Cited

U.S. PATENT DOCUMENTS

| | | | |
|---|---|---|---|
| 4,148,830 A | 4/1979 | Pruett et al. | |
| 4,241,216 A | 12/1980 | Bergman et al. | |
| 4,314,947 A * | 2/1982 | Hohenschutz | C07C 67/08 202/158 |
| 4,421,695 A * | 12/1983 | Parsons | C07C 41/18 558/92 |
| 4,426,524 A | 1/1984 | Plummer | |
| 5,288,918 A | 2/1994 | Maher et al. | |
| 5,434,313 A | 7/1995 | Harrison et al. | |
| 7,799,942 B2 | 9/2010 | Osborne et al. | |
| 2004/0030175 A1 * | 2/2004 | Disteldorf | C07C 67/08 560/98 |
| 2007/0161815 A1 * | 7/2007 | Osborne | C07C 67/08 560/76 |
| 2010/0130767 A1 * | 5/2010 | De Munck | C07C 67/08 560/99 |
| 2011/0218285 A1 * | 9/2011 | Stockl | C08L 93/04 524/308 |
| 2011/0251420 A1 | 10/2011 | Disteldorf et al. | |

FOREIGN PATENT DOCUMENTS

| | | |
|---|---|---|
| DE | 1 593 368 A1 | 7/1970 |
| DE | 2 139 630 A1 | 2/1973 |
| DE | 2 244 373 A1 | 4/1974 |
| DE | 24 04 855 A1 | 8/1975 |
| DE | 24 45 303 A1 | 4/1976 |
| DE | 26 28 987 A1 | 1/1978 |
| DE | 32 28 881 A1 | 2/1984 |
| EP | 0 366 089 A2 | 5/1990 |
| EP | 0 695 734 A1 | 2/1996 |
| EP | 0 880 494 B1 | 5/2000 |
| EP | 1 047 655 B1 | 5/2003 |
| GB | 2312673 * | 11/1997 |
| JP | 62-267341 A | 11/1987 |
| JP | 6-122652 A | 5/1994 |
| JP | 6-157407 A | 6/1994 |
| JP | H08-71429 A | 3/1996 |
| JP | 2001-072629 A | 3/2001 |
| JP | 2002-155026 A | 5/2002 |
| JP | 2003-160535 A | 6/2003 |
| JP | 2003-165913 A | 6/2003 |
| JP | 2009-191051 A | 8/2009 |
| JP | 2010-523560 A | 7/2010 |
| KR | 2009-0089266 A | 8/2009 |
| RU | 1004351 A1 | 3/1983 |
| WO | WO 95/14647 A1 | 6/1995 |
| WO | WO 98/23566 A1 | 6/1998 |
| WO | WO 00/78702 A1 | 12/2000 |
| WO | WO 01/14297 A1 | 3/2001 |
| WO | WO 01/87809 A1 | 11/2001 |
| WO | WO 02/083695 A1 | 10/2002 |

(Continued)

OTHER PUBLICATIONS

Lutropur pp. 1-4 (Year: 2011).*

(Continued)

*Primary Examiner* — Jafar F Parsa
*Assistant Examiner* — Blaine G Doletski
(74) *Attorney, Agent, or Firm* — Oblon, McClelland, Maier & Neustadt, L.L.P.

(57) ABSTRACT

The present invention relates to a process for the production of carboxylic esters by reaction of carboxylic acids and/or carboxylic anhydrides with at least one alcohol selected from alkanols having at least 5 carbon atoms, cycloalkanols, and alkoxy-alkanols, in the presence of an acidic esterification catalyst. The invention further relates to the use of the resultant carboxylic esters as plasticizers or in a plasticizer composition for thermoplastic polymers and elastomers.

17 Claims, 1 Drawing Sheet

(56) References Cited

FOREIGN PATENT DOCUMENTS

| WO | WO 2005/028407 A1 | 3/2005 |
|---|---|---|
| WO | WO 2008/123928 A1 | 10/2008 |
| WO | WO 2010/076192 A1 | 7/2010 |

OTHER PUBLICATIONS

International Search Report dated Feb. 12, 2015 in PCT/EP2014/073272.

English translation of International Preliminary Report on Patentability and Written Opinion dated May 3, 2016 in PCT/EP2014/073272.

David F. Cadogan, et al., "Plasticizers" Ullmann's Encyclopedia of Industrial Chemistry, vol. 27, XP055167665, 2012, pp. 599-618.

Peter M. Lorz, et al., "Phthalic Acid and Derivatives" Ullmann's Encyclopedia of Industrial Chemistry, vol. 27, 2012, pp. 131-180.

Japanese Office Action dated Feb. 20, 2017 in corr. Japanese Patent Application No. 2016-527373 (w/ English translation).

Chang Xia et al., "The Preparation and Applications of Environmentally-friendly Plasticizer DOTP", Biomass Chemical Engineering, 2012, vol. 46, No. 6, pp. 1-7 (w/ English Abstract).

Jia Chang-ying, "Producing Mixed Plasticizer from TA Residue", Guangxi Chemical Industry, Mar. 1999, vol. 28, No. 1, pp. 54-57 (w/ English Abstract).

Chen Su et al., "Preparation of DOTP with dodecylbenzene sulfonic acid as catalyst", Journal of Nanjing University of Chemical Technology, Jul. 1997, vol. 19, No. 3, pp. 91-94 (w/ English Abstract).

Chloe Action (Notification of Reason for Refusal) dated Sep. 27, 2017 in Korean Patent Application No. 10-2016-7014332 with English translation.

U.S. Appl. No. 14/411,670, filed Dec. 29, 2014, US 2015/0166926 A1, Scherer, et al.

U.S. Appl. No. 14/443,742, filed May 19, 2015, US 2015/0299607 A1, Scherer, et al.

U.S. Appl. No. 14/443,769, filed May 19, 2015, US 2015/0307807 A1, Scherer, et al.

U.S. Appl. No. 14/783,707, filed Oct. 9, 2015, US 2016/0075671 A1, Wagner, et al.

\* cited by examiner

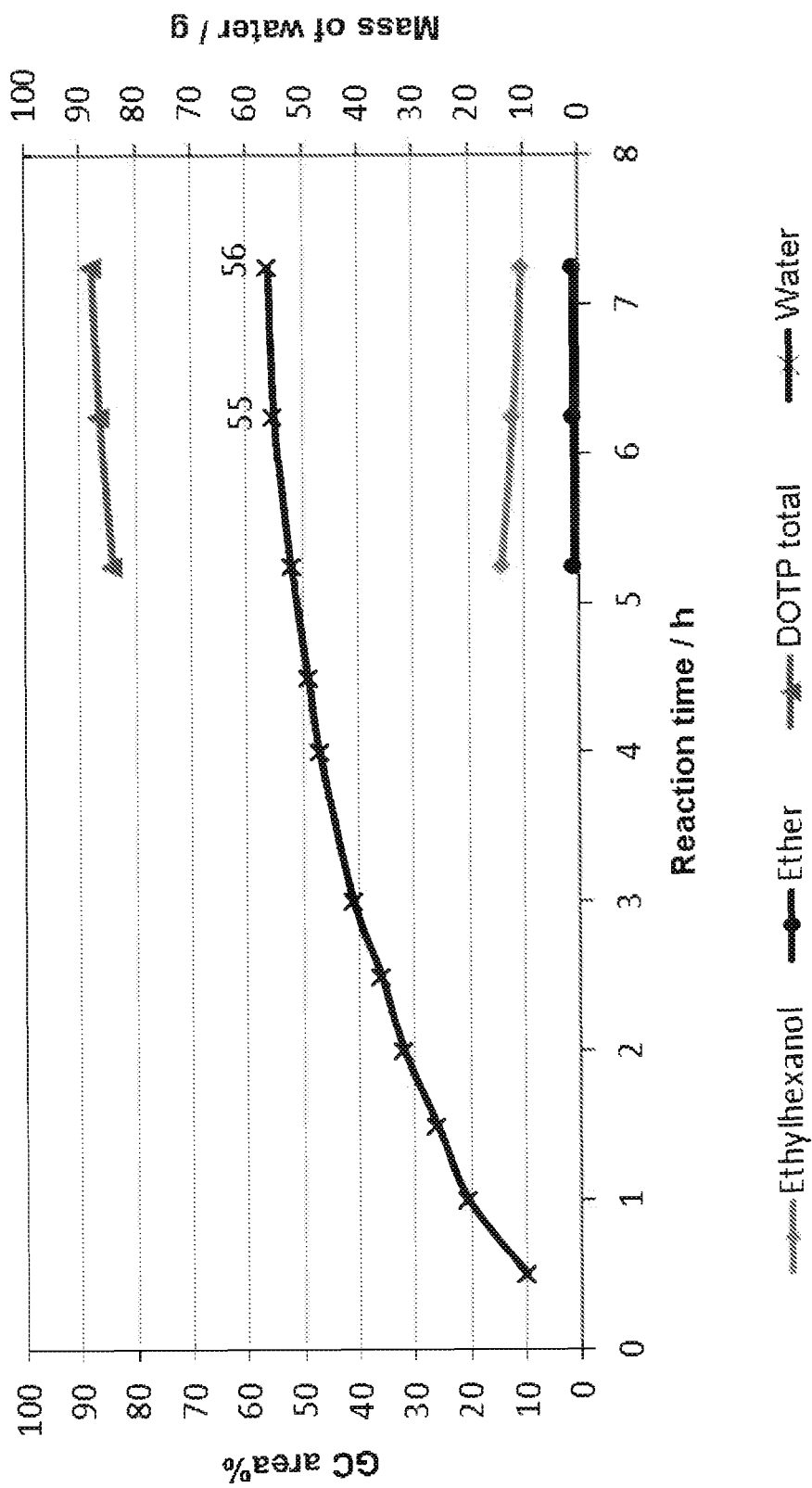

METHOD FOR PRODUCING CARBOXYLIC ACID ESTERS AND THE USE THEREOF AS PLASTICIZERS

BACKGROUND OF THE INVENTION

The present invention relates to a process for the production of carboxylic esters by reaction of carboxylic acids and/or carboxylic anhydrides with at least one alcohol selected from alkanols having at least 5 carbon atoms, cycloalkanols, and alkoxy-alkanols, in the presence of an acidic esterification catalyst. The invention further relates to the use of the resultant carboxylic esters as plasticizers or in a plasticizer composition for thermoplastic polymers and elastomers.

PRIOR ART

Esters of aliphatic and aromatic carboxylic acids with alkanols, cycloalkanols, or alkoxyalkanols are widely used in industry. They are by way of example widely used in surface-coating resins and as constituents of paints, and it is specifically the esters of acetic acid, phthalic acid, trimellitic acid, terephthalic acid, adipic acid, sebacic acid, or maleic acid that are used here. They are moreover specifically suitable as plasticizers or as component of a plasticizer composition for thermoplastic polymers and elastomers.

Plasticizers are added to a wide variety of plastics in order to achieve the desired processing properties or the desired usage properties, the aim being to render the plastics softer, more flexible, and/or more extensible. The use of plasticizers generally serves to shift the thermoplastic range of plastics toward lower temperatures, so that the desired resilient properties can be obtained in the region of low processing temperatures and low usage temperatures. Important thermoplastic polymers in which plasticizers are usually used are not only polyvinyl chloride (PVC) but also by way of example polyvinyl butyral (PVB), styrene homo- and copolymers, polyacrylates, polysulfides, and thermoplastic polyurethanes (PU). Materials that have been widely used as plasticizers in the past because of their good compatibility with PVC and with other polymers, and because of their advantageous performance characteristics, are phthalic diesters with alcohols of varying chemical structure, an example being diethylhexyl phthalate (DEHP). However, these give rise to some toxicological concerns and in recent times they have been replaced by other plasticizers specifically for sensitive application sectors such as toys, food packaging, and medical items. Particular materials of importance here are the esters of other aromatic carboxylic acids, for example of terephthalic acid, trimellitic acid, and benzoic acid.

It is known that carboxylic esters can be produced by reaction of carboxylic acids with alcohols. This reaction can be carried out autocatalytically or with catalysis, for example by Brønsted acids or by Lewis acids. Processes of this type are described in Lorz et al., Phthalic Acid and Derivatives, Ullmann's Encyclopedia of Industrial Chemistry, 2007, pages 131-180 (DOI: 10.1002/14356007.a20_181.pub2). In the case of autocatalytic esterification the reaction temperatures are usually >200° C. Nevertheless, conversions achieved are generally only partial, and recycling of the residual carboxylic acid is therefore essential.

Irrespective of the nature of the catalysis, there is always a resultant temperature-dependent equilibrium between the starting materials (carboxylic acid and alcohol) and the products (ester and water). The reaction of internal carboxylic anhydrides with alcohols proceeds in two steps: alcoholysis of the anhydride to give the monoester generally proceeds rapidly and to completion. Further reaction of the monoester to give the diester with formation of water of reaction is reversible and proceeds slowly. This second step is the rate-determining step of the reaction. In order to shift the equilibrium in favor of the ester (or of the full ester in the case of polybasic acids), an entrainer is generally used to remove the water of reaction from the mixture. If one of the starting materials (alcohol or carboxylic acid) has a lower boiling point than the resultant ester and has a region of emiscibility with water, a starting material can be used as entrainer and, after removal of water, can be returned to the mixture. In the case of esterification of higher aliphatic carboxylic acids, aromatic carboxylic acids, or di- or polybasic carboxylic acids, the entrainer is generally the alcohol used.

Typical esterification catalysts for the production of carboxylic esters suitable as plasticizers are tetraalkyl titanates.

U.S. Pat. No. 7,799,942 by way of example discloses a process for the production of diesters of terephthalic acid, for example bis(2-ethylhexyl) terephthalate (DOTP) in which terephthalic acid and a $C_6$-$C_{10}$-alcohol are subjected to esterification in the presence of a tetraalkyl titanate as catalyst, where the water produced during the esterification reaction, and a portion of the alcohol, are removed by passing an inert gas through the reaction zone, or with the aid of a distillation column.

The use of tetraalkyl titanates as catalysts has a number of attendant disadvantages: in order to remove the catalyst, a base, for example aqueous NaOH, is admixed with the reaction mixture, and the resultant hydrolysis products are removed by filtration. This removal is time-consuming, and space-time yields achieved are therefore low. Further work-up of the reaction mixture is generally required, for example distillation for the removal of excess alcohol and/or treatment with activated carbon in order to achieve acceptable color values.

Other materials described in the prior art as catalysts for the production of carboxylic esters are mineral acids and strong organic acids, for example methanesulfonic acid and p-toluenesulfonic acid. However, Lorz et al., Phthalic Acid and Derivatives, Ullmann's Encyclopedia of Industrial Chemistry, 2007, pages 131-180 (DOI: 10.1002/14356007.a20_181.pub2) teaches that Brønsted acid catalysts can be used only up to a temperature of 165° C., since otherwise disruptive side reactions occur and can inter alia lead to formation of olefins through elimination of water from the alcohols used, and to formation of strongly colored byproducts.

WO 2010/076192 describes a process for the production of carboxylic esters by reaction of a carboxylic acid or of a carboxylic anhydride or of a mixture thereof with an alcohol in the presence of an esterification catalyst, in which the water of reaction produced during the esterification reaction is removed by distillation in the form of alcohol-water azeotrope with the vapor. The vapor is at least to some extent condensed and subjected to phase separation, and the organic phase is at least to some extent returned to the reaction system, and components which have lower boiling points than the alcohol used for the esterification reaction are removed here from the phase that is to be returned. A very wide variety of amphiphilic metal catalysts, and also mineral acids and organic acids, are mentioned as suitable esterification catalyst. A specific description is provided of the continuous production of diisononyl phthalate and dipropylheptyl phthalate, using a mixture of isopropyl titanate and n-butyl titanate as esterification catalyst.

JP 62267341 discloses a process for the production of carboxylic esters for use as plasticizers, obtainable by reaction of a carboxylic acid with an alcohol in the presence of a sulfonic acid as esterification catalyst. The crude esterification product here is subjected to purification by addition of a base, e.g. CaO or MgO, and of a solid adsorbent, for example activated carbon, kieselguhr, or activated bleaching earth, in order to reduce the acid number and, respectively, the color value.

JP 1994157407 discloses a process for the production of carboxylic esters by reaction of a carboxylic acid with an alcohol in the presence of methanesulfonic acid as esterification catalyst at a low reaction temperature of from 80 to 120° C., where the water of reaction is selectively removed from the reaction mixture with use of a water-permeable membrane. The production of bis(2-ethylhexyl) phthalate is described as specific embodiment.

JP 1994122652 describes a process for the production of carboxylic esters by reaction of a carboxylic acid or of a carboxylic anhydride with an alcohol in the presence of a sulfonic acid as esterification catalyst and of a zeolite for the binding of the water of reaction formed during the esterification reaction. The production of bis(2-ethylhexyl) phthalate from phthalic anhydride and 2-ethylhexanol at a reaction temperature of 100° C. in the presence of methanesulfonic acid as catalyst is specifically described, and uses zeolite sodium A or zeolite HY as water-binding agent.

WO 2008/123928 describes a process for the production of di(n-butyl) terephthalate from terephthalic acid and n-butanol, where the esterification reaction is carried out with a 1.25- to 4-fold molar excess of n-butanol at atmospheric pressure and at a reaction temperature of from 110 to 220° C. with use of an esterification catalyst. Specifically, because the boiling point of n-butanol is 117° C., this process is preferably carried out at a reaction temperature of from 115 to 150° C. (i.e. in essence at reflux), preference being given here to use of a sulfonic acid or sulfuric acid as esterification catalyst. n-Butanol is continuously introduced into the reaction zone during the reaction. The water produced during the reaction is extracted by distillation in the form of azeotropic mixture. In some of the embodiments, nitrogen is passed through the reaction mixture, but this measure has no discernible favorable effect on the yield, purity, or color value of the resultant esterification product.

The present invention is based on the object of providing an improved process for the production of carboxylic esters which are suitable for a use as plasticizer. The intention here is preferably to achieve conversion that is as far as possible complete after a short reaction time, and thus to achieve a high space-time yield. A further intention is that it be possible to carry out the process at low cost and in a technically simple manner, e.g. by using an inexpensive catalyst and by avoiding complicated work-up steps, thus permitting substantial avoidance of the disadvantages described above which result inter alia from the use of tetraalkyl titanates as esterification catalysts. The resultant carboxylic esters are nevertheless intended to feature good product properties, specifically for a use as plasticizer. These include, for applications in sectors where the optical properties of the plasticized plastics are important, minimized coloring of the carboxylic esters, apparent by way of example in a low color value.

Surprisingly, it has now been found that this object is achieved when the esterification reaction for the production of the carboxylic esters suitable as plasticizers is carried out at high temperatures in the presence of an organic sulfonic acid, specifically methanesulfonic acid, as catalyst, and in the presence of an inert gas, where the alcohol used for the esterification reaction serves as entrainer for the resultant water of reaction and, after water removal, is returned to the reaction. In one specific embodiment, methanesulfonic acid with low total chlorine content and low sulfate content is used as catalyst.

BRIEF DESCRIPTION OF THE INVENTION

The invention provides a process for the production of carboxylic esters, in which a reaction mixture which comprises at least one carboxylic acid and/or at least one carboxylic anhydride, and which comprises at least one alcohol $R^1$—OH, and/or at least one alcohol $R^2$—[O—X]$_n$—OH, in which $R^1$ is selected from unbranched and branched $C_5$-$C_{13}$-alkyl moieties and $C_5$-$C_6$-cycloalkyl moieties, where the cycloalkyl moieties are unsubstituted or can be substituted by at least one $C_1$-$C_{10}$-alkyl moiety, $R^2$ is selected from unbranched $C_1$-$C_{13}$-alkyl moieties and branched $C_3$-$C_{13}$-alkyl moieties, X is an unbranched $C_2$-$C_5$-alkylene group or branched $C_3$-$C_5$-alkylene group, and n has the value 1, 2, or 3, is reacted in a reaction system composed of one or more reactors, with the proviso that the reaction takes place in the presence of at least one catalyst selected from organic sulfonic acids, with introduction, into the reaction system, of a gas that is inert under the reaction conditions, at a reaction mixture temperature from 125° C. to 240° C., and with distillative removal, in the form of an azeotropic mixture with the alcohol $R^1$—OH and/or $R^2$—[O—X]$_n$—OH used, of at least one portion of the water formed during the reaction, where at least to some extent the alcohol $R^1$—OH and/or $R^2$—[O—X]$_n$—OH removed by distillation is returned to the reaction system.

One preferred embodiment of the invention provides a process for the production of carboxylic esters, in which a reaction mixture which comprises at least one carboxylic acid and/or at least one carboxylic anhydride, and which comprises at least one alcohol $R^1$—OH, in which $R^1$ is selected among unbranched and branched $C_5$-$C_{13}$-alkyl moieties and $C_5$-$C_6$-cycloalkyl moieties, where the cycloalkyl moieties are unsubstituted or can be substituted by at least one $C_1$-$C_{10}$-alkyl moiety, is reacted in a reaction composed of one or more reactors, with the proviso that the reaction takes place in the presence of at least one catalyst selected among organic sulfonic acids, with introduction, into the reaction system, of a gas that is inert under the reaction conditions, at a reaction mixture temperature of from 125 to 240° C., and with distillative removal, in the form of an azeotropic mixture with the alcohol $R^1$—OH used, of at least one portion of the water formed during the reaction, where at least to some extent the alcohol $R^1$—OH removed by distillation is returned to the reaction system.

In one specific embodiment, the process of the invention serves for the production of esters of terephthalic acid, very specifically for the production of bis(2-ethylhexyl) terephthalate (DOTP) via reaction of terephthalic acid with 2-ethylhexanol.

In another specific embodiment, the process of the invention serves for the production of esters of acetic acid with alkoxyalkanols, very specifically for the production of 2-butoxyethyl acetate, 2-(2-butoxyethoxy)ethyl acetate, 1-methoxy-2-propyl acetate, and 3-methoxypropyl acetate via reaction of 2-butoxyethanol, 2-(2-butoxyethoxy)-ethanol, 1-methoxy-2-propanol, or 3-methoxypropanol with acetic acid or acetic anhydride.

The invention further provides the use of the resultant carboxylic esters as plasticizers or as component in a plasticizer composition for thermoplastic polymers and elastomers.

DESCRIPTION OF THE INVENTION

The process of the invention has the following advantages:
  It is possible to produce carboxylic esters suitable as plasticizers in short reaction times, i.e. with high space-time yield.
  Despite the relatively severe reaction conditions, the carboxylic esters are obtained in high yields and with good selectivities.
  Although a Brønsted acid is used as catalyst, very little formation of undesired byproducts, specifically of ethers of the alcohol used for the esterification reaction, and of olefins from elimination of water from the alcohol, is observed.
  It is generally possible to omit the use of complicated measures for purification of the carboxylic esters obtained according to the process of the invention. This applies specifically to the use of adsorbents for obtaining less-colored products.
  It is generally possible to omit the use of external organic solvents, i.e. the use of components which act as solvents and which differ from the starting materials used for the production of the carboxylic esters and from the products formed in the reaction.
  The process of the invention is specifically suitable for the production of esters of terephthalic acid, trimellitic acid, and benzoic acid, and of esters of alicyclic and aliphatic carboxylic acids which because of their advantageous toxicological properties are of great importance for use as plasticizers.
  The resultant carboxylic esters have no, or only slight, coloring, and feature a low Hazen color value (determinable in accordance with DIN/EN/ISO 6271-2). This is generally at least as good as, or better than, that of products which are obtained by the substantially more complicated process by means of catalysis by tetraalkyl titanates.

For the purposes of the present invention, the expression "$C_1$-$C_{10}$-alkyl" comprises unbranched alkyl groups having from 1 to 10 carbon atoms, and also branched alkyl groups having from 3 to 10 carbon atoms. Among these are methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethyl-propyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, isooctyl, 2-ethylhexyl, n-nonyl, isononyl, 2-propylhexyl, n-decyl, isodecyl, 2-propylheptyl, and the like. It is preferable that the groups here are unbranched $C_1$-$C_8$-alkyl groups or branched $C_3$-$C_8$-alkyl groups. It is particularly preferable that the groups here are unbranched $C_1$-$C_5$-alkyl groups or branched $C_3$-$C_5$-alkyl groups.

The expression "$C_5$-$C_{13}$-alkyl" comprises unbranched and branched $C_5$-$C_{13}$-alkyl groups. It is preferable that $C_5$-$C_{13}$-alkyl is selected from n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 2-methylhexyl, 1-ethylpentyl, 2-ethylpentyl, 1-propylbutyl, 1-ethyl-2-methylpropyl, n-octyl, isooctyl, 2-ethylhexyl, n-nonyl, isononyl, 2-propylhexyl, n-decyl, isodecyl, 2-propylheptyl, n-undecyl, isoundecyl, n-dodecyl, isododecyl, n-tridecyl and isotridecyl, and the like. It is particularly preferable that $C_5$-$C_{13}$-alkyl is n-octyl, n-nonyl, isononyl, 2-ethylhexyl, isodecyl, 2-propylheptyl, n-undecyl, isoundecyl, n-tridecyl, and isotridecyl. The expression "$C_1$-$C_{13}$-alkyl" comprises unbranched alkyl groups having from 1 to 13 carbon atoms, and also branched alkyl groups having from 3 to 13 carbon atoms. It is preferable that $C_1$-$C_{13}$-alkyl is selected from methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 2-methylhexyl, 1-ethylpentyl, 2-ethylpentyl, 1-propylbutyl, 1-ethyl-2-methylpropyl, n-octyl, isooctyl, 2-ethylhexyl, n-nonyl, isononyl, 2-propylhexyl, n-decyl, isodecyl, 2-propylheptyl, n-undecyl, isoundecyl, n-dodecyl, isododecyl, n-tridecyl, or isotridecyl, and the like. It is particularly preferable that $C_1$-$C_{13}$-alkyl is unbranched $C_1$-$C_9$-alkyl groups, or branched $C_3$-$C_9$-alkyl groups, in particular methyl, ethyl, propyl, n-butyl, n-pentyl, n-hexyl, n-heptyl, n-octyl, 2-ethylhexyl, n-nonyl, or isononyl.

The definition of the expression "$C_1$-$C_{13}$-alkyl" also includes the expressions "$C_3$-$C_{13}$-alkyl", "$C_1$-$C_9$-alkyl", and "$C_3$-$C_9$-alkyl".

The expression "$C_5$-$C_6$-cycloalkyl" comprises for the purposes of the present invention cyclic hydrocarbons having from 5 to 6, in particular having 6, carbon atoms. Among these are cyclopentyl and cyclohexyl.

Substituted $C_5$-$C_6$-cycloalkyl groups can, as appropriate to their ring size, have one or more (e.g. 1, 2, 3, 4, or 5) $C_1$-$C_{10}$-alkyl substituents. Examples of $C_5$-$C_6$-cycloalkyl groups are 2- and 3-methylcyclopentyl, 2- and 3-ethylcyclopentyl, 2-, 3- and 4-methyl-cyclohexyl, 2-, 3-, and 4-ethylcyclohexyl, 2-, 3-, and 4-propylcyclohexyl, 2-, 3-, and 4-isopropylcyclohexyl, 2-, 3-, and 4-butylcyclohexyl, 2-, 3-, and 4-sec-butylcyclohexyl, and 2-, 3-, and 4-tert-butylcyclohexyl, and the like.

For the purposes of the present invention, the expression "$C_2$-$C_5$-alkylene" comprises unbranched divalent hydrocarbon moieties having from 2 to 5 carbon atoms, and also branched divalent hydrocarbon moieties having from 3 to 5 carbon atoms. Among these are by way of example 1,2- ethylene, 1,3-propylene, 1,2-propylene, 1-methyl-1,2-ethylene, 1,4-butylene, 1-methyl-1,3-propylene, 2-methyl-1,3-propylene, 1,5-pentylene, 1-methyl-1,4-butylene, 2-methyl-1,4-butylene, and the like. It is preferable that "$C_2$-$C_5$-alkylene" is unbranched $C_2$-$C_4$-alkylene groups or branched $C_3$-$C_4$-alkylene groups, particularly 1,2-ethylene and 1,3-propylene.

The definition of the expression "$C_2$-$C_5$-alkylene" also includes the expressions "$C_3$-$C_5$-alkylene", "$C_2$-$C_4$-alkylene", "$C_3$-$C_4$-alkylene", and "$C_2$-$C_3$-alkylene".

For the purposes of the invention, the expression "reaction system" means a reactor or an arrangement of a plurality of reactors. A plurality of reactors are preferably arranged in series. The process of the invention can be carried out batchwise or continuously, but is preferably carried out continuously.

The reactors can be any desired reactors suitable for the conduct of liquid-phase chemical reactions.

Suitable reactors are non-backmixing reactors, for example tubular reactors or holding containers provided with internals, but preferably backmixing reactors, such as stirred tanks, loop reactors, or jet loop reactors. However, it is also possible to use combinations of successive backmixing reactors and non-backmixing reactors.

It is also optionally possible to combine a plurality of reactors in a multistage apparatus. These reactors are by way of example loop reactors with internal perforated plates, cascaded containers, tubular reactors with intermediate feed, or stirred columns.

Stirred-tank reactors are preferably used. The stirred-tank reactors are mostly composed of metallic materials, preference being given here to stainless steel. It is preferable that a stirrer or a circulating pump is used for vigorous mixing of the reaction mixture.

In one preferred embodiment, the process of the invention is carried out in a single stirred tank. In another preferred embodiment, the process of the invention is carried out in at least two stirred tanks connected to one another in the form of a cascade. Specifically in the case of continuous conduct of the process, it can be advantageous for maximum conversion to connect a plurality of reactors in the form of a cascade. The reaction mixture passes through the individual reactors in succession, and the outflow from the first reactor here is introduced into the second reactor, the outflow from the second reactor is introduced into the third reactor, etc. The cascade can by way of example comprise from 2 to 10 reactors, a preferred number of reactors here being 2, 3, 4 or 5.

In the case of batchwise conduct of the process, carboxylic acid and/or carboxylic anhydride and alcohol $R^1$—OH and/or $R^2$—[O—X]$_n$—OH and the catalyst can be charged simultaneously or in succession to the reactor. The catalyst can be introduced in pure form or as solution, preferably dissolved in one of the starting materials, at the start or only after the reaction temperature has been reached. Carboxylic anhydrides often react with alcohols autocatalytically, i.e. without catalysis, to give the corresponding ester acids (hemiesters), an example being phthalic anhydride giving the phthalic monoester. A catalyst is therefore often required only after the first reaction step.

In the case of continuous conduct of the process, streams of the starting materials and of the catalyst are introduced into the reactor or, if a reactor cascade is used, preferably into the first reactor of the cascade. The residence time in the reactor or in the individual reactors here is determined by the volume of the reactors and the flow rate of the starting materials.

The process of the invention takes place with introduction, to the reaction system, of a gas that is inert under the reaction conditions. To this end, the inert gas can be passed into the gas space of the reaction system or into the liquid reaction mixture. The introduction of the inert gas into the reaction system preferably takes place in a manner that creates a large area for interchange between the liquid reaction mixture and the inert gas. The treatment with the inert gas during the reaction has a stripping effect and completes the removal of the water of reaction. It is moreover possible to introduce energy into the reaction system by introducing a heated inert gas. In this embodiment, the introduction of energy by way of the reactor jacket can be reduced accordingly. It is thus advantageously possible to reduce any overheating of the reaction mixture in the vicinity of the reactor jacket, and to reduce the formation of byproducts.

In preferred embodiments, the inert gas is introduced into the boiling reaction mixture below the liquid surface in such a way that it bubbles through the reaction mixture. The pressure of the inert gas must be sufficiently high to overcome the hydrostatic pressure of the reaction mixture above the inert gas feed. By way of example, it is possible to introduce the inert gas from 20 to 50 cm below the liquid surface of the reaction mixture.

The inert gas can be fed into the system by way of any desired suitable apparatuses. Among these are by way of example nozzles for gas-supply lances. The nozzles can be on the base of the reactor or in the vicinity of the base. To this end, the nozzles can be designed as apertures of a hollow chamber surrounding the reactor. A possible alternative use is immersed nozzles with suitable supply lines. By way of example, there can be a plurality of nozzles arranged in the form of a ring. The nozzles can point upward or downward. The nozzles preferably point obliquely downward.

It is preferable that the reaction mixture is mixed in order to bring about an interchange of reaction mixture in the reactor region below the feed of the inert gas with reaction mixture in the reactor region above the feed of the inert gas. By way of example, stirrers or a circulating pump are suitable for the mixing process. In one specific variant, what is known as a gas-introducing stirrer is used for the introduction of the inert gas and for the mixing of the reaction mixture.

If the process of the invention is carried out in at least two stirred tanks connected to one another in the form of a cascade, it is preferable that the inert gas passes through all of the reactors of the cascade. If more than one reactor is treated with the inert gas, this can be conducted in parallel to the individual reactors, or the inert gas can pass through a plurality of reactors in succession. It is also possible to design combinations in which fresh inert gas bubbles through two or more reactors, and the vapor comprising the inert gas is passed from at least one of the reactors through at least one further reactor.

By way of example, fresh inert gas can be introduced into the final reactor in the direction of flow, and in a cascade of n reactors, the vapor comprising the inert gas can be collected from the nth reactor and introduced in the form of vapor into the reaction mixture in reactor (n−1, etc.).

The esterification reaction takes place according to the invention in the presence of an inert gas. The expression "inert gas" means a gas which, under the prevailing process conditions, does not enter into any reactions with the starting materials, reagents, or solvents involved in the reaction, or with the resultant products. Examples of suitable inert gases are nitrogen, helium, argon etc. It is preferable to use nitrogen as inert gas.

According to the invention, the process takes place with distillative removal of at least one portion of the water formed during the reaction, in the form of an azeotropic mixture with the alcohol $R^1$—OH and/or $R^2$—$[O—X]_n$—OH used, which is then at least to some extent returned to the reaction system. To this end, a vapor is removed from the reaction system and is condensed, the condensate is separated into an aqueous phase and an alcohol phase, and the alcohol phase is at least to some extent returned to the reaction system. "Return to the reaction system" means that the alcohol phase is passed into any desired at least one reactor of the reaction system.

Any of the suitable condensers can be used for the condensation or partial condensation of the vapor. These can be cooled by any desired coolants. Preference is given to condensers with air cooling and/or water cooling, particular preference being given here to air cooling.

The resultant condensate is subjected to phase separation to give an aqueous phase and an organic phase. For this, the condensate is usually passed into a phase separator (decanter) where mechanical settling causes it to break down into two phases which can be extracted separately. The aqueous phase is removed and can, optionally after treatment, be discarded or used as stripping water in the post-treatment of the ester.

The vapor from the individual reactors of a cascade can be combined, and the resultant combined material can be condensed. It is optionally possible in each case to combine a plurality of reactors of the cascade to give a subunit, in which case then each subunit has a condenser coupled thereto. There is also moreover the possibility of coupling each reactor of the cascade to a condenser.

The alcohol phase to be returned can be passed into any desired reactor of a cascade, or can be divided over a plurality of reactors of the cascade. However, it is preferable that the alcohol phase to be returned is not passed into the final reactor of the cascade. It is preferable that the alcohol phase to be returned is passed exclusively or mainly into the first reactor of the cascade.

There are various possibilities for the return of the alcohol phase into the reaction system. In one possibility, the organic phase is, optionally after heating, pumped into the liquid reaction mixture.

For thermal optimization of the process, the alcohol phase can be returned by way of a column (known as return-alcohol column) into the reaction system. In said return-alcohol column, the returned alcohol phase is conducted in counterflow to at least a portion of the vapor. The alcohol phase is advantageously introduced into the return-alcohol column at the top or in the upper region. The outflow of condensate from the return-alcohol column passes back into the reaction system. When a reactor cascade is used, the outflow of condensate from the return-alcohol column is preferably introduced into the first reactor. The return of the alcohol phase by way of the return-alcohol column has the advantage that the returned alcohol phase is preheated and is freed from traces of water which have remained in the organic phase after phase separation or which are dissolved in the organic phase in accordance with their thermodynamic solubility. The return-alcohol column can by way of example be a plate column, packed column, or filled column. A small number of theoretical plates is generally sufficient. By way of example, a suitable column has from 2 to 10 theoretical plates. When a reactor cascade is used, it is preferable that the vapor leaves at least the first reactor by way of the return-alcohol column. One or more, or all of the, further reactors can likewise have a vapor outlet to the return-alcohol column.

The at least one alcohol $R^1$—OH and/or the at least one alcohol $R^2$—$[O—X]_n$—OH is preferably used in a stoichiometric excess with respect to the carboxy groups. It is assumed here that a carboxylic anhydride has two carboxy groups requiring esterification. It is particularly preferable that the at least one alcohol $R^1$—OH and/or $R^2$—$[O—X]_n$—OH is used in a 1 to 100% molar excess, in particular in a 5 to 50% molar excess, specifically in a 7 to 15% molar excess.

The amount preferably used of the catalyst is from 0.5 to 5 mol %, particularly from 1 to 2 mol %, based on the molar amount of carboxy groups.

It is preferable that the esterification catalyst is selected from methanesulfonic acid and toluenesulfonic acid. In particular, methanesulfonic acid is used as esterification catalyst. The catalyst can be used in the form of pure substance or in the form of an aqueous solution.

For the purposes of the present invention, the expression "total chlorine content" means the sum of the content of free chlorine and the content of chlorine bonded in organic or inorganic form.

The methanesulfonic acid used preferably has a total chlorine content of at most 20 ppm, preferably at most 5 ppm, in particular at most 1 ppm.

The methanesulfonic acid used preferably has a sulfate content of at most 50 ppm, preferably at most 20 ppm.

A particularly suitable pure methanesulfonic acid is obtainable by the process described in WO 0050351. This type of pure MSA is obtainable commercially as Lutropur® from BASF SE, either in the form of 70% aqueous solution (Lutropur® MSA) or in the form of anhydrous MSA (Lutropur® MSA100).

The esterification reaction is preferably carried out in the temperature range from 130 to 235° C., in particular from 135 to 230° C. According to the process of the invention, the esterification reaction can also be carried out at even higher temperatures, specifically at least 150° C., more specifically at least 170° C.

The ideal temperatures depend on the starting materials, on the progress of the reaction, and on the catalyst concentration. They can easily be determined for any individual case by experiments. In order to remove the water of reaction it is necessary that the alcohol can be removed by distillation from the reaction mixture. The desired temperature or the desired temperature range can be adjusted through the pressure in the reactor. In the case of low-boiling-point alcohols it is therefore possible to carry out the reaction at superatmospheric pressure or ambient pressure, and in the case of higher-boiling-point alcohols it is therefore possible to carry out the reaction at reduced pressure.

If the esterification reaction uses a cascade made of a plurality of reactors, it is possible that all of the reactors of a cascade are operated at the same temperature. However, it is generally preferable to increase the temperature continuously from the first to the final reactor of a cascade, the temperature at which a reactor is operated being the same as or higher than that of the reactor situated upstream in the direction of flow of the reaction mixture. All of the reactors can advantageously be operated at in essence the same pressure.

The esterification reaction preferably takes place at ambient pressure or at reduced pressure. It is preferable to carry out the esterification reaction at a pressure of from 0.001 to 2.0 bar, particularly from 0.01 to 1.1 bar.

The esterification reaction can be carried out in the absence of any external solvent or in the presence of an organic solvent. It is preferable to carry out the esterification reaction in the absence of any external solvent.

If the esterification reaction is carried out in the presence of an external solvent, this is preferably an organic solvent that is inert under the reaction conditions. Among these are by way of example aliphatic hydrocarbons, halogenated aliphatic hydrocarbons, aromatic and substituted aromatic hydrocarbons, and ethers. It is preferable that the solvent is selected from pentane, hexane, heptane, ligroin, petroleum ether, cyclohexane, dichloromethane, trichloromethane, tetrachloromethane, benzene, toluene, xylene, chlorobenzene, dichlorobenzenes, dibutyl ether, THF, dioxane, and mixtures thereof.

Once the reaction has ended, the reaction mixture, which consists essentially of the desired ester and of excess alcohol, comprises small amounts of ester carboxylic acid(s) and/or unreacted carboxylic acid, alongside the catalyst and/or downstream products thereof.

These crude ester mixtures are worked up by removing the excess alcohol, neutralizing the acidic compounds, and removing the resultant solid byproducts. The sequence of the process steps here can be varied. Most of the unreacted alcohol is removed here by distillation at atmospheric pressure or in vacuo. The final traces of the alcohol can by way of example be removed by steam distillation, in particular in the temperature range from 120 to 225° C. in vacuo. The removal of the alcohol can be a first or a final work-up step.

The neutralization of the acidic substances, such as carboxylic acids, ester carboxylic acids, or optionally the acidic catalysts, is achieved by adding bases, e.g. alkali metal carbonates and/or alkaline earth metal carbonates, alkali metal hydrogencarbonates, alkaline earth metal hydrogencarbonates, or alkali metal hydroxides or alkaline earth metal hydroxides. The neutralizing agent can be used in solid form or preferably in the form of solution, in particular in the form of aqueous solution. Aqueous sodium hydroxide solution is often used here at a concentration of from 1 to 30% by weight, preferably from 20 to 30% by weight. The amount added of the neutralizing agent is from one to four times, in particular from one to two times, the stoichiometrically required amount determined by titration.

The distillation process also removes the ether of the alcohol $R^1$—OH used and/or of the alcohol $R^2$—[O—X]$_n$—OH used, to the extent that said ether is present. The amount of this ether comprised in the reaction mixtures obtained after the process of the invention is generally <2% by weight, preferably <1% by weight (determined by GC measurements on derivatized samples). The resultant ether can, if desired, be converted by acidic ether cleavage back to the alcohol $R^1$—OH or, respectively, back to the alcohol $R^2$—[O—X]$_n$—OH.

The excess alcohol $R^1$—OH and/or $R^2$—[O—X]$_n$—OH can be directly reused, or can be further purified, e.g. by means of distillation.

The resultant carboxylic ester is in essence free from solid contaminants. However, it can be subjected to filtration in order to remove any substances that may be present in suspension in the reactor.

Preferred alcohols $R^1$—OH are $C_5$-$C_{13}$-alkanols. The $C_5$-$C_{13}$-alkanols can be straight-chain or branched, or be composed of mixtures of straight-chain and branched $C_5$-$C_{13}$-alkanols. Among the preferred $C_5$-$C_{13}$-alkanols are by way of example n-pentanol, 2-methylbutanol, n-hexanol, n-heptanol, isoheptanol, n-octanol, isooctanol, 2-ethylhexanol, n-nonanol, isononanol, isodecanol, 2-propylheptanol, n-undecanol, isoundecanol, n-dodecanol, isododecanol, n-tridecanol, and isotridecanol, and also mixtures thereof. Particular preference is given to $C_7$-$C_{12}$-alkanols.

$C_7$-$C_{12}$-alkanols particularly preferred as alcohols $R^1$—OH can be straight-chain or branched or be composed of mixtures of straight-chain and branched $C_7$-$C_{12}$-alkanols. Among the particularly preferred $C_7$-$C_{12}$-alkanols are by way of example n-octanol, 2-ethylhexanol, n-nonanol, isononanol, isodecanol, 2-propylheptanol, n-undecanol, isoundecanol, and n-dodecanol, and also mixtures thereof. In particular, 2-ethylhexanol is used as alcohol in the process of the invention.

Preference is further given to use of $C_5$-$C_6$-cycloalkanols, and also of $C_5$-$C_{13}$-alkanols, as alcohols $R^1$—OH. The $C_5$-$C_6$-cycloalkanols are selected from cyclopentanol and cyclohexanol, and also mixtures thereof. Cyclohexanol is preferred. Substituted $C_5$-$C_6$-cycloalkanols can, as appropriate to their ring size, have one or more (e.g. 1, 2, 3, 4, or 5) $C_1$-$C_{10}$-alkyl substituents. Examples of $C_5$-$C_6$-cycloalkanols are 2- and 3-methylcyclopentanol, 2- and 3-ethylcyclopentanol, 2-, 3- and 4-methylcyclohexanol, 2-, 3-, and 4-ethylcyclohexanol, 2-, 3-, and 4-propylcyclohexanol, 2-, 3-, and 4-isopropylcyclohexanol, 2-, 3-, and 4-butylcyclohexanol, 2-, 3-, and 4-sec-butylcyclohexanol, and 2-, 3-, and 4-tert-butylcyclohexanol.

Particularly preferred $C_7$-$C_{12}$-alkanols are defined in more detail below.

Heptanol

The heptanols used in the process of the invention can be straight-chain or branched or can be composed of mixtures of straight-chain and branched heptanols. It is preferable to use mixtures of branched heptanols, also known as isoheptanol, which are produced via rhodium- or preferably cobalt-catalyzed hydroformylation of propene dimer, obtainable by way of example by the Dimersol® process, and subsequent hydrogenation of the resultant isoheptanals to give an isoheptanol mixture. Because of the process used for its production, the resultant isoheptanol mixture is composed of a plurality of isomers. Substantially straight-chain heptanols can be obtained via rhodium- or preferably cobalt-catalyzed hydroformylation of 1-hexene and subsequent hydrogenation of the resultant n-heptanal to give n-heptanol. The hydroformylation of 1-hexene or of propene dimer can be achieved by methods known per se: compounds used as catalyst in hydroformylation with rhodium catalysts homogeneously dissolved in the reaction medium can be not only uncomplexed rhodium carbonyl compounds which are formed in situ under the conditions of the hydroformylation reaction within the hydroformylation reaction mixture on exposure to synthesis gas, e.g. from rhodium salts, but also complex rhodium carbonyl compounds, in particular complexes with organic phosphines, such as triphenylphosphine, or with organophosphites, preferably chelating biphosphites, as described by way of example in U.S. Pat. No. 5,288,918. Compounds used in the cobalt-catalyzed hydroformylation of these olefins are generally cobalt carbonyl compounds which are homogeneously soluble in the reaction mixture and which are formed in situ from cobalt salts under the conditions of the hydroformylation reaction on exposure to synthesis gas. If the cobalt-catalyzed hydroformylation is carried out in the presence of trialkyl- or triarylphosphines, the desired heptanols are formed directly as hydroformylation product, and there is therefore then no need for further hydrogenation of the aldehyde function.

Examples of suitable processes for the cobalt-catalyzed hydroformylation of 1-hexene or of the hexene isomer mixtures are the established industrial processes explained on pages 162-168 of Falbe, New Syntheses with Carbon Monoxide, Springer, Berlin, 1980, an example being the Ruhrchemie process, the BASF process, the Kuhlmann process, or the Shell process. Whereas the Ruhrchemie, BASF, and Kuhlmann process operate with non-ligand-modified cobalt carbonyl compounds as catalysts and thus give hexanal mixtures, the Shell process (DE-A 1593368) uses, as catalyst, phosphine- or phosphite-ligand-modified cobalt carbonyl compounds which lead directly to the hexanol mixtures because they also have high hydrogenation activity. DE-A 2139630, DE-A 2244373, DE-A 2404855, and WO 01014297 provide detailed descriptions of advantageous embodiments for the conduct of the hydroformylation with non-ligand-modified cobalt carbonyl complexes.

The rhodium-catalyzed hydroformylation of 1-hexene or of the hexene isomer mixtures can use the established industrial low-pressure rhodium hydroformylation process with triphenylphosphine-ligand-modified rhodium carbonyl compounds, which is subject matter of U.S. Pat. No. 4,148, 830. Non-ligand-modified rhodium carbonyl compounds can serve advantageously as catalyst for the rhodium-catalyzed hydroformylation of long-chain olefins, for example of the hexene isomer mixtures obtained by the processes described above; this differs from the low-pressure process in requiring a higher pressure of from 80 to 400 bar. The conduct of high-pressure rhodium hydroformylation processes of this type is described by way of example in EP-A 695734, EP-B 880494, and EP-B 1047655.

The isoheptanal mixtures obtained after hydroformylation of the hexene isomer mixtures are catalytically hydrogenated in a manner that is per se conventional to give isoheptanol mixtures. For this purpose it is preferable to use heterogeneous catalysts which comprise, as catalytically active component, metals and/or metal oxides of group VI to VIII, or else of transition group I, of the periodic table of the elements, in particular chromium, molybdenum, manganese, rhenium, iron, cobalt, nickel, and/or copper, optionally deposited on a support material, such as $Al_2O_3$, $SiO_2$ and/or $TiO_2$. Catalysts of this type are described by way of example in DE-A 3228881, DE-A 2628987, and DE-A 2445303. It is particularly advantageous to carry out the hydrogenation of the isoheptanals with an excess of hydrogen of from 1.5 to 20% above the stoichiometric amount of hydrogen needed for the hydrogenation of the isoheptanals, at temperatures of from 50 to 200° C., and at a hydrogen pressure of from 25 to 350 bar, and for avoidance of side-reactions to add, during the course of the hydrogenation, in accordance with DE-A 2628987, a small amount of water, advantageously in the form of an aqueous solution of an alkali metal hydroxide or alkali metal carbonate, in accordance with the teaching of WO 01087809.

Octanol

For many years, 2-ethylhexanol was the largest-production-quantity plasticizer alcohol, and it can be obtained through the aldol condensation of n-butyraldehyde to give 2-ethylhexanal and subsequent hydrogenation thereof to give 2-ethylhexanol (see Ullmann's Encyclopedia of Industrial Chemistry; $5^{th}$ edition, vol. A 10, pp. 137-140, VCH Verlagsgesellschaft GmbH, Weinheim 1987).

Substantially straight-chain octanols can be obtained via rhodium- or preferably cobalt-catalyzed hydroformylation of 1-heptene and subsequent hydrogenation of the resultant n-octanal to give n-octanol. The 1-heptene needed for this purpose can be obtained from the Fischer-Tropsch synthesis of hydrocarbons.

By virtue of the production route used for the alcohol isooctanol, it is not a unitary chemical compound, in contrast to 2-ethylhexanol or n-octanol, but instead is an isomer mixture of variously branched $C_8$-alcohols, for example of 2,3-dimethyl-1-hexanol, 3,5-dimethyl-1-hexanol, 4,5-dimethyl-1-hexanol, 3-methyl-1-heptanol, and 5-methyl-1-heptanol; these can be present in the isooctanol in various quantitative proportions which depend on the production conditions and production processes used. Isooctanol is usually produced via codimerization of propene with butenes, preferably n-butenes, and subsequent hydroformylation of the resultant mixture of heptene isomers. The octanal isomer mixture obtained in the hydroformylation can subsequently be hydrogenated to give the isooctanol in a manner that is conventional per se.

The codimerization of propene with butenes to give isomeric heptenes can advantageously be achieved with the aid of the homogeneously catalyzed Dimersol® process (Chauvin et al; Chem. Ind.; May 1974, pp. 375-378), which uses, as catalyst, a soluble nickel phosphine complex in the presence of an ethylaluminum chloride compound, for example ethylaluminum dichloride. Examples of phosphine ligands that can be used for the nickel complex catalyst are tributylphosphine, triisopropyl-phosphine, tricyclohexyl-phosphine, and/or tribenzylphosphine. The reaction takes place at temperatures of from 0 to 80° C., and it is advantageous here to set a pressure at which the olefins are present in solution in the liquid reaction mixture (Cornils; Hermann: Applied Homogeneous Catalysis with Organometallic Compounds; $2^{nd}$ edition, vol. 1; pp. 254-259, Wiley-VCH, Weinheim 2002).

In an alternative to the Dimersol® process operated with nickel catalysts homogeneously dissolved in the reaction medium, the codimerization of propene with butenes can also be carried out with a heterogeneous NiO catalyst deposited on a support; heptene isomer distributions obtained here are similar to those obtained in the homogeneously catalyzed process. Catalysts of this type are by way of example used in what is known as the Octol® process (Hydrocarbon Processing, February 1986, pp. 31-33), and a specific heterogeneous nickel catalyst with good suitability for olefin dimerization or olefin codimerization is disclosed by way of example in WO 9514647.

Codimerization of propene with butenes can also use, instead of nickel-based catalysts, heterogeneous Brønsted-acid catalysts; heptenes obtained here are generally more highly branched than in the nickel-catalyzed processes. Examples of catalysts suitable for this purpose are solid phosphoric acid catalysts, e.g. phosphoric-acid-impregnated kieselguhr or diatomaceous earth, these being as utilized in the PolyGas® process for olefin dimerization or olefin oligomerization (Chitnis et al; Hydrocarbon Engineering 10, No. 6-June 2005). Brønsted-acid catalysts that have very good suitability for the codimerization of propene and butenes to give heptenes are zeolites, which are used in the EMOGAS® process, a further development based on the PolyGas® process.

The 1-heptene and the heptene isomer mixtures are converted to n-octanal and, respectively, octanal isomer mixtures by the known processes explained above in connection with the production of n-heptanal and heptanal isomer mixtures, by means of rhodium- or cobalt-catalyzed hydroformylation, preferably cobalt-catalyzed hydroformylation. These are then hydrogenated to give the corresponding octanols, for example by means of one of the catalysts mentioned above in connection with production of n-heptanol and of isoheptanol.

Nonanol

Substantially straight-chain nonanol can be obtained via rhodium- or preferably cobalt-catalyzed hydroformylation of 1-octene and subsequent hydrogenation of the resultant n-nonanal. The starting olefin 1-octene can be obtained by way of example by way of ethylene oligomerization by means of a nickel complex catalyst that is homogenously soluble in the reaction medium—1,4-butanediol—with, for example, diphenyl-phosphinoacetic acid or 2-diphenylphosphinobenzoic acid as ligand. This process is also known as the Shell Higher Olefins Process or SHOP process (see Weisermel, Arpe: Industrielle Organische Chemie [Industrial organic chemistry]; 5$^{th}$ edition, p. 96; Wiley-VCH, Weinheim 1998).

The alcohol component isononanol used in the process of the invention is not a unitary chemical compound, but instead is a mixture of variously branched, isomeric $C_9$-alcohols which can have various degrees of branching, depending on the manner in which they were produced, and also in particular on the starting materials used. The isononanols are generally produced via dimerization of butenes to give isooctene mixtures, subsequent hydroformylation of the isooctene mixtures, and hydrogenation of the resultant isononanal mixtures to give isononanol mixtures, as explained in Ullmann's Encyclopedia of Industrial Chemistry, 5$^{th}$ edition, vol. A1, pp. 291-292, VCH Verlagsgesellschaft GmbH, Weinheim 1995.

Isobutene, cis- and trans-2-butene, and also 1-butene, or a mixture of these butene isomers, can be used as starting material for the production of the isononanols. The dimerization of pure isobutene, mainly catalyzed by means of liquid Brønsted acids, e.g. sulfuric acid or phosphoric acid, or by means of solid Brønsted acids, e.g. phosphoric acid absorbed on kieselguhr, $SiO_2$, or $Al_2O_3$, as support material, or zeolites, mainly gives the highly branched compound 2,4,4-trimethylpentene, also termed diisobutylene, which gives highly branched isononanols after hydroformylation and hydrogenation of the aldehyde.

Preference is given to isononanols with a low degree of branching. Isononanol mixtures of this type with little branching are obtained from the linear butenes 1-butene, and cis- and/or trans-2-butene which optionally can also comprise relatively small amounts of isobutene, by way of the route described above involving butene dimerization, hydroformylation of the isooctene, and hydrogenation of the resultant isononanal mixtures. A preferred raw material is what is known as raffinate II, which is obtained from the $C_4$-cut of a cracker, for example of a steam cracker, after elimination of allenes, acetylenes, and dienes, in particular 1,3-butadiene, via partial hydrogenation thereof to give linear butenes, or removal thereof via extractive distillation, for example by means of N-methylpyrrolidone, and subsequent Brønsted-acid catalyzed removal of the isobutene comprised therein via reaction thereof with methanol or isobutanol by established large-scale-industrial processes with formation of the fuel additive methyl tert-butyl ether (MTBE), or of the isobutyl tert-butyl ether that is used to obtain pure isobutene.

Raffinate II also comprises, alongside 1-butene and cis- and trans-2-butene, n- and isobutane, and residual amounts of up to 5% by weight of isobutene.

The dimerization of the linear butenes or of the butene mixture comprised in raffinate II can be carried out by means of the familiar processes used on a large industrial scale, for example those explained above in connection with the production of isoheptene mixtures, for example by means of heterogeneous, Brønsted-acid catalysts such as those used in the PolyGas® process or EMOGAS® process, by means of the Dimersol® process with use of nickel complex catalysts homogeneously dissolved in the reaction medium, or by means of heterogeneous, nickel(II)-oxide-containing catalysts by the Octol® process or by the process of WO 9514647. The resultant isooctene mixtures are converted to isononanal mixtures by the known processes explained above in connection with the production of heptanal isomer mixtures, by means of rhodium or cobalt-catalyzed hydroformylation, preferably cobalt-catalyzed hydroformylation. These are then hydrogenated to give the suitable isononanol mixtures, for example by means of one of the catalysts mentioned above in connection with the production of isoheptanol.

The resultant isononanol isomer mixtures can be characterized by way of their iso-index, which can be calculated from the degree of branching of the individual, isomeric isononanol components in the isononanol mixture multiplied by the percentage proportion of these in the isononanol mixture: by way of example, n-nonanol contributes the value 0 to the iso-index of an isononanol mixture, methyloctanols (single branching) contribute the value 1, and dimethylheptanols (double branching) contribute the value 2. The higher the linearity, the lower is the iso-index of the relevant isononanol mixture. Accordingly, the iso-index of an isononanol mixture can be determined via gas-chromatographic separation of the isononanol mixture into its individual isomers and attendant quantification of the percentage quantitative proportion of these in the isononanol mixture, determined by standard methods of gas-chromatographic analysis. In order to increase the volatility of the isomeric nonanols and improve the gas-chromatographic separation of these, they are advantageously trimethylsilylated by means of standard methods, for example via reaction with N-methyl-N-trimethylsilyltrifluoracetamide, prior to gas-chromatographic analysis. In order to achieve maximum quality of separation of the individual components during gas-chromatographic analysis, it is preferable to use capillary columns with polydimethylsiloxane as stationary phase. Capillary columns of this type are obtainable commercially, and a little routine experimentation by the person skilled in the art is all that is needed in order to select, from the many different products available commercially, one that has ideal suitability for this separation task.

The isononanols used in the process of the invention are generally isononanols with an iso index of from 0.8 to 2, preferably from 1.0 to 1.8, and particularly preferably from 1.1 to 1.5, esterified or etherified, which can be produced by the abovementioned processes.

Possible compositions of the type of isononanol mixtures that can be used in the process of the invention are stated below merely by way of example, and it should be noted here that the proportions of the isomers individually listed within the isononanol mixture can vary, depending on the composition of the starting material, for example raffinate II, the composition of butenes in which can vary with the production process, and on variations in the production conditions used, for example in the age of the catalysts utilized, and conditions of temperature and of pressure, which have to be adjusted appropriately thereto.

By way of example, an isononanol mixture produced via cobalt-catalyzed hydroformylation and subsequent hydrogenation from an isooctene mixture produced with use of raffinate II as raw material by means of the catalyst and process in accordance with WO 9514647 can have the following composition:

from 1.73 to 3.73% by weight, preferably from 1.93 to 3.53% by weight, particularly preferably from 2.23 to 3.23% by weight of 3-ethyl-6-methyl-hexanol;
from 0.38 to 1.38% by weight, preferably from 0.48 to 1.28% by weight, particularly preferably from 0.58 to 1.18% by weight of 2,6-dimethylheptanol;
from 2.78 to 4.78% by weight, preferably from 2.98 to 4.58% by weight, particularly preferably from 3.28 to 4.28% by weight of 3,5-dimethylheptanol;
from 6.30 to 16.30% by weight, preferably from 7.30 to 15.30% by weight, particularly preferably from 8.30 to 14.30% by weight of 3,6-dimethylheptanol;
from 5.74 to 11.74% by weight, preferably from 6.24 to 11.24% by weight, particularly preferably from 6.74 to 10.74% by weight of 4,6-dimethylheptanol;
from 1.64 to 3.64% by weight, preferably from 1.84 to 3.44% by weight, particularly preferably from 2.14 to 3.14% by weight of 3,4,5-trimethylhexanol;
from 1.47 to 5.47% by weight, preferably from 1.97 to 4.97% by weight, particularly preferably from 2.47 to 4.47% by weight of 3,4,5-trimethylhexanol, 3-methyl-4-ethylhexanol and 3-ethyl-4-methylhexanol;
from 4.00 to 10.00% by weight, preferably from 4.50 to 9.50% by weight, particularly preferably from 5.00 to 9.00% by weight of 3,4-dimethylheptanol;
from 0.99 to 2.99% by weight, preferably from 1.19 to 2.79% by weight, particularly preferably from 1.49 to 2.49% by weight of 4-ethyl-5-methylhexanol and 3-ethylheptanol;
from 2.45 to 8.45% by weight, preferably from 2.95 to 7.95% by weight, particularly preferably from 3.45 to 7.45% by weight of 4,5-dimethylheptanol and 3-methyloctanol;
from 1.21 to 5.21% by weight, preferably from 1.71 to 4.71% by weight, particularly preferably from 2.21 to 4.21% by weight of 4,5-dimethylheptanol;
from 1.55 to 5.55% by weight, preferably from 2.05 to 5.05% by weight, particularly preferably from 2.55 to 4.55% by weight of 5,6-dimethylheptanol;
from 1.63 to 3.63% by weight, preferably from 1.83 to 3.43% by weight, particularly preferably from 2.13 to 3.13% by weight of 4-methyloctanol;
from 0.98 to 2.98% by weight, preferably from 1.18 to 2.78% by weight, particularly preferably from 1.48 to 2.48% by weight of 5-methyloctanol;
from 0.70 to 2.70% by weight, preferably from 0.90 to 2.50% by weight, particularly preferably from 1.20 to 2.20% by weight of 3,6,6-trimethylhexanol;
from 1.96 to 3.96% by weight, preferably from 2.16 to 3.76% by weight, particularly preferably from 2.46 to 3.46% by weight of 7-methyloctanol;
from 1.24 to 3.24% by weight, preferably from 1.44 to 3.04% by weight, particularly preferably from 1.74 to 2.74% by weight of 6-methyloctanol;
from 0.1 to 3% by weight, preferably from 0.2 to 2% by weight, particularly preferably from 0.3 to 1% by weight of n-nonanol;
from 25 to 35% by weight, preferably from 28 to 33% by weight, particularly preferably from 29 to 32% by weight of other alcohols having 9 and 10 carbon atoms; with the proviso that the entirety of the components mentioned gives 100% by weight.

In accordance with what has been said above, an isononanol mixture produced via cobalt-catalyzed hydroformylation and subsequent hydrogenation with use of an isooctene mixture produced by means of the PolyGas® process or EMOGAS® process with an ethylene-containing butene mixture as raw material can vary within the range of the compositions below, depending on the composition of the raw material and variations in the reaction conditions used:

from 6.0 to 16.0% by weight, preferably from 7.0 to 15.0% by weight, particularly preferably from 8.0 to 14.0% by weight of n-nonanol;
from 12.8 to 28.8% by weight, preferably from 14.8 to 26.8% by weight, particularly preferably from 15.8 to 25.8% by weight of 6-methyloctanol;
from 12.5 to 28.8% by weight, preferably from 14.5 to 26.5% by weight, particularly preferably from 15.5 to 25.5% by weight of 4-methyloctanol;
from 3.3 to 7.3% by weight, preferably from 3.8 to 6.8% by weight, particularly preferably from 4.3 to 6.3% by weight of 2-methyloctanol;
from 5.7 to 11.7% by weight, preferably from 6.3 to 11.3% by weight, particularly preferably from 6.7 to 10.7% by weight of 3-ethylheptanol;
from 1.9 to 3.9% by weight, preferably from 2.1 to 3.7% by weight, particularly preferably from 2.4 to 3.4% by weight of 2-ethylheptanol;
from 1.7 to 3.7% by weight, preferably from 1.9 to 3.5% by weight, particularly preferably from 2.2 to 3.2% by weight of 2-propylhexanol;
from 3.2 to 9.2% by weight, preferably from 3.7 to 8.7% by weight, particularly preferably from 4.2 to 8.2% by weight of 3,5-dimethylheptanol;
from 6.0 to 16.0% by weight, preferably from 7.0 to 15.0% by weight, particularly preferably from 8.0 to 14.0% by weight of 2,5-dimethylheptanol;
from 1.8 to 3.8% by weight, preferably from 2.0 to 3.6% by weight, particularly preferably from 2.3 to 3.3% by weight of 2,3-dimethylheptanol;
from 0.6 to 2.6% by weight, preferably from 0.8 to 2.4% by weight, particularly preferably from 1.1 to 2.1% by weight of 3-ethyl-4-methylhexanol;
from 2.0 to 4.0% by weight, preferably from 2.2 to 3.8% by weight, particularly preferably from 2.5 to 3.5% by weight of 2-ethyl-4-methylhexanol;
from 0.5 to 6.5% by weight, preferably from 1.5 to 6% by weight, particularly preferably from 1.5 to 5.5% by weight of other alcohols having 9 carbon atoms; with the proviso that the entirety of the components mentioned gives 100% by weight.

Decanol

The alcohol component isodecanol used in the process of the invention is not a unitary chemical compound, but instead is a complex mixture of variously branched, isomeric decanols.

These are generally produced via nickel- or Brønsted-acid-catalyzed trimerization of propylene, for example by the PolyGas® process or the EMOGAS® process explained above, subsequent hydroformylation of the resultant isononene isomer mixture by means of homogeneous rhodium or cobalt carbonyl catalysts, preferably by means of cobalt carbonyl catalysts, and hydrogenation of the resultant isodecanal isomer mixture, e.g. by means of the catalysts and processes mentioned above in connection with the production of $C_7$-$C_9$-alcohols (Ullmann's Encyclopedia of Industrial Chemistry; 5$^{th}$ edition, vol. A1, p. 293, VCH Verlagsgesellschaft GmbH, Weinheim 1985). The resultant isodecanol generally has a high degree of branching.

The 2-propylheptanol used in the process of the invention can be pure 2-propylheptanol or can be a propylheptanol isomer mixture of the type generally formed during the industrial production of 2-propylheptanol and generally also called 2-propylheptanol.

Pure 2-propylheptanol can be obtained via aldol condensation of n-valeraldehyde and subsequent hydrogenation of the resultant 2-propylheptanal, for example in accordance with U.S. Pat. No. 2,921,089. By virtue of the production process, commercially obtainable 2-propylheptanol generally comprises, alongside the main component 2-propylheptanol, one or more of the following isomers of 2-propylheptanol: 2-propyl-4-methylhexanol, 2-propyl-5-methylhexanol, 2-isopropylheptanol, 2-isopropyl-4-methylhexanol, 2-isopropyl-5-methylhexanol, and/or 2-propyl-4,4-dimethylpentanol. The presence of other isomers of 2-propylheptanol, for example 2-ethyl-2,4-dimethylhexanol, 2-ethyl-2-methylheptanol, and/or 2-ethyl-2,5-dimethylhexanol, in the 2-propylheptanol is possible, but because the rates of formation of the aldehydic precursors of these isomers in the aldol condensation are low, the amounts of these present in the 2-propylheptanol are only trace amounts, if they are present at all, and they play practically no part in determining the plasticizer properties of the compounds produced from these 2-propylheptanol isomer mixtures.

Various hydrocarbon sources can be utilized as starting material for the production of 2-propylheptanol, for example 1-butene, 2-butene, raffinate I—an alkane/alkene mixture which is obtained from the $C_4$-cut of a cracker after removal of allenes, of acetylenes, and of dienes and which also comprises, alongside 1- and 2-butene, considerable amounts of isobutene—or raffinate II, which is obtained from raffinate I via removal of isobutene and then comprises, as olefin components other than 1- and 2-butene, only small proportions of isobutene. It is also possible, of course, to use mixtures of raffinate I and raffinate II as raw material for the production of 2-propylheptanol. These olefins or olefin mixtures can be hydroformylated by methods that are per se conventional with cobalt or rhodium catalysts, and 1-butene here gives a mixture of n- and isovaleraldehyde—the term isovaleraldehyde designating the compound 2-methylbutanal, the n/iso ratio of which can vary within relatively wide limits, depending on catalyst used and on hydroformylation conditions. By way of example, when a triphenylphosphine-modified homogeneous rhodium catalyst (Rh/TPP) is used, n- and isovaleraldehyde are formed in an n/iso ratio that is generally from 10:1 to 20:1 from 1-butene, whereas when rhodium hydroformylation catalysts modified with phosphite ligands are used, for example in accordance with U.S. Pat. No. 5,288,918 or WO 05028407, or when rhodium hydroformylation catalysts modified with phosphoamidite ligands are used, for example in accordance with WO 0283695, n-valeraldehyde is formed almost exclusively. While the Rh/TPP catalyst system converts 2-butene only very slowly in the hydroformylation, and most of the 2-butene can therefore be reclaimed from the hydroformylation mixture, 2-butene is successfully hydroformylated with the phosphite-ligand- or phosphorus amidite ligand-modified rhodium catalysts mentioned, the main product formed being n-valeraldehyde. In contrast, isobutene comprised within the olefinic raw material is hydroformylated at varying rates by practically all catalyst systems to 3-methylbutanal and, in the case of some catalysts, to a lesser extent to pivalaldehyde.

The $C_5$-aldehydes obtained in accordance with starting materials and catalysts used, i.e. n-valeraldehyde optionally mixed with isovaleraldehyde, 3-methylbutanal, and/or pivalaldehyde, can be separated, if desired, completely or to some extent by distillation into the individual components prior to the aldol condensation, and here again there is therefore a possibility of influencing and of controlling the composition of isomers of the $C_{10}$-alcohol component used in the production process of the invention. Equally, it is possible that the $C_5$-aldehyde mixture formed during the hydroformylation is introduced into the aldol condensation without prior isolation of individual isomers. If n-valeraldehyde is used in the aldol condensation, which can be carried out by means of a basic catalyst, for example an aqueous solution of sodium hydroxide or of potassium hydroxide, for example by the processes described in EP-A 366089, U.S. Pat. No. 4,426,524, or U.S. Pat. No. 5,434,313, 2-propylheptanal is produced as sole condensate, whereas if a mixture of isomeric $C_5$-aldehydes is used the product comprises an isomer mixture of the products of the homoaldol condensation of identical aldehyde molecules and of the crossed aldol condensation of different valeraldehyde isomers. The aldol condensation can, of course, be controlled via targeted reaction of individual isomers in such a way that a single aldol condensation isomer is formed predominantly or entirely. The relevant aldol condensates can then be hydrogenated with conventional hydrogenation catalysts, for example those mentioned above for the hydrogenation of aldehydes, to give the corresponding alcohols or alcohol mixtures, usually after preceding, preferably distillative isolation from the reaction mixture and, if desired, distillative purification.

The process of the invention generally uses mixtures of the 2-propylheptanol with the propylheptanol isomers mentioned in which the content of 2-propylheptanol is at least 50% by weight, preferably from 60 to 98% by weight, and particularly preferably from 80 to 95% by weight, in particular from 85 to 95% by weight.

Suitable mixtures of 2-propylheptanol with the propylheptanol isomers comprise by way of example those of from 60 to 98% by weight of 2-propylheptanol, from 1 to 15% by weight of 2-propyl-4-methylhexanol, and from 0.01 to 20% by weight of 2-propyl-5-methylhexanol, and from 0.01 to 24% by weight of 2-isopropylheptanol, where the sum of the proportions of the individual constituents does not exceed 100% by weight. It is preferable that the proportions of the individual constituents give a total of 100% by weight.

Other suitable mixtures of 2-propylheptanol with the propylheptanol isomers comprise by way of example those of from 75 to 95% by weight of 2-propylheptanol, from 2 to 15% by weight of 2-propyl-4-methylhexanol, from 1 to 20% by weight of 2-propyl-5-methylhexanol, from 0.1 to 4% by weight of 2-isopropylheptanol, from 0.1 to 2% by weight of 2-isopropyl-4-methylhexanol, and from 0.1 to 2% by weight of 2-isopropyl-5-methylhexanol, where the sum of the proportions of the individual constituents does not exceed 100% by weight. It is preferable that the proportions of the individual constituents give a total of 100% by weight.

Preferred mixtures of 2-propylheptanol with the propylheptanol isomers comprise those with from 85 to 95% by weight of 2-propylheptanol, from 5 to 12% by weight of 2-propyl-4-methylhexanol, and from 0.1 to 2% by weight of 2-propyl-5-methylhexanol, and from 0.01 to 1% by weight of 2-isopropylheptanol, where the sum of the proportions of the individual constituents does not exceed 100% by weight. It is preferable that the proportions of the individual constituents give a total of 100% by weight.

When said 2-propylheptanol isomer mixtures are used instead of pure 2-propylheptanol, the isomer composition of the alkyl ester groups of the products is practically the same as the composition of the propylheptanol isomer mixtures used for the esterification.

Undecanol

The undecanols used in the process of the invention can be straight-chain or branched, or can be composed of mixtures of straight-chain and branched undecanols. It is preferable to use, as alcohol component, mixtures of branched undecanols, also termed isoundecanol.

Substantially straight-chain undecanol can be obtained via rhodium- or preferably cobalt-catalyzed hydroformylation of 1-decene and subsequent hydrogenation of the resultant n-undecanal. The starting olefin 1-decene is produced by way of the SHOP process mentioned previously for the production of 1-octene.

For the production of branched isoundecanol, the 1-decene obtained in the SHOP process can be subjected to skeletal isomerization, for example by means of acidic zeolitic molecular sieves, as described in WO 9823566, whereupon mixtures of isomeric decenes are formed, rhodium- or preferably cobalt-catalyzed hydroformylation of which, with subsequent hydrogenation of the resultant isoundecanal mixtures, gives the isoundecanol used for the production of the compounds of the invention. Hydroformylation of 1-decene or of isodecene mixtures by means of rhodium or cobalt catalysis can be achieved as described previously in connection with the synthesis of $C_7$-$C_{10}$-alcohols. Similar considerations apply to the hydrogenation of n-undecanal or of isoundecanal mixtures to give n-undecanol and, respectively, isoundecanol.

After distillative purification of the hydrogenation product, the resultant $C_7$-$C_{11}$-alkyl alcohols or a mixture of these can be used in the process of the invention.

Dodecanol

Substantially straight-chain dodecanol can be obtained advantageously by way of the Alfol® process or Epal® process. These processes include the oxidation and hydrolysis of straight-chain trialkylaluminum compounds which are constructed stepwise by way of a plurality of ethylation reactions, starting from triethylaluminum, with use of Ziegler-Natta catalysts. The desired n-dodecanol can be obtained from the resultant mixtures of substantially straight-chain alkyl alcohols of varying chain length after distillative discharge of the $C_{12}$-alkyl alcohol fraction.

Alternatively, n-dodecanol can also be produced via hydrogenation of natural fatty acid methyl esters, for example from coconut oil.

Branched isododecanol can be obtained by analogy with the processes described previously for the codimerization and/or oligomerization of olefins with subsequent hydroformylation and hydrogenation of the isoundecene mixtures. After distillative purification of the hydrogenation product, the resultant isododecanols or mixtures of these, as described above, can be used in the process of the invention.

In one preferred embodiment of the process of the invention, the alkoxyalkanols are selected from compounds of the general formula $R^2$—[O—X]$_n$—OH where $R^2$ is selected from unbranched $C_1$-$C_9$-alkyl moieties and branched $C_3$-$C_9$-alkyl moieties, X is an unbranched $C_2$-$C_3$-alkylene group or a branched $C_3$-$C_4$-alkylene group, and n has the value 1 or 2.

It is particularly preferable that the alcohol $R^2$—[O—X]$_n$—OH is selected from 2-butoxyethanol, 2-(2-butoxyethoxy)ethanol, 1-methoxy-2-propanol, 3-methoxypropanol, or a mixture thereof.

The carboxylic acids and/or carboxylic anhydrides used in the process of the invention are selected from aromatic mono-, di-, tri-, or tetracarboxylic acids, aliphatic mono- and dicarboxylic acids, hydroxycarboxylic acids, alicyclic mono-, di-, tri-, and tetracarboxylic acids, heterocyclic dicarboxylic acids, the anhydrides of the abovementioned carboxylic acids, and mixtures thereof.

The aromatic mono-, di-, tri-, or tetracarboxylic acids and anhydrides of these used in the process of the invention are by way of example benzoic acid, benzoic anhydride, phthalic acid, phthalic anhydride, isophthalic acid, terephthalic acid, trimellitic acid, trimellitic anhydride, pyromellitic acid, and pyromellitic dianhydride.

The aliphatic mono- and dicarboxylic acids used in the process of the invention are by way of example saturated mono- and dicarboxylic acids such as acetic acid, butyric acid, valeric acid, succinic acid, adipic acid, or sebacic acid, saturated mono- and dicarboxylic acids such as acrylic acid, maleic acid, or fumaric acid, or else optionally the anhydrides of the abovementioned carboxylic acids.

The hydroxycarboxylic acids used in the process of the invention are by way of example glycolic acid, lactic acid, malic acid, tartaric acid, or citric acid, or else optionally anhydrides of these.

The alicyclic mono-, di-, tri-, and tetracarboxylic acids used in the process of the invention are by way of example the ring-hydrogenated derivatives of the abovementioned aromatic mono-, di-, tri-, or tetracarboxylic acids, an example being cyclohexanecarboxylic acid, 1,2-cyclohexanedicarboxylic acid, 1,3-cyclohexanedicarboxylic acid, 1,4-cyclohexanedicarboxylic acid, 1,2,4-cyclohexanedicarboxylic acid, or 1,2,4,5-cyclohexanetetracarboxylic acid, or else optionally anhydrides of these.

The heterocyclic dicarboxylic acids used in the process of the invention are by way of example 2,5-furandicarboxylic acid or 2,5-tetrahydrofurandicarboxylic acid.

In one preferred embodiment of the process of the invention, the carboxylic acid and/or the carboxylic anhydride is selected from acetic acid, acetic anhydride, benzoic acid, benzoic anhydride, phthalic acid, phthalic anhydride, isophthalic acid, terephthalic acid, trimellitic acid, trimellitic anhydride, pyromellitic acid, and pyromellitic dianhydride. It is particularly preferable that the carboxylic acid and/or the carboxylic anhydride is selected from acetic acid, acetic anhydride, benzoic acid, benzoic anhydride, terephthalic acid, trimellitic acid, trimellitic anhydride. In particular, acetic acid, acetic anhydride or terephthalic acid is used as carboxylic acid or, respectively, carboxylic anhydride in the process of the invention.

Plasticizer Use

In plastics where optical properties are of prime importance it is generally desirable that the plasticizers used for production thereof have little intrinsic color, i.e. a low color value.

The carboxylic esters produced by the process of the invention feature in particular a low color value. They are therefore advantageously suitable for the use as plasticizers or in plasticizers for thermoplastic polymers and elastomers.

Furthermore, the use of high-purity methanesulfonic acid (Lutropur® MSA or Lutropur® MSA 100) as catalyst gives the carboxylic esters produced by the process of the invention low total chlorine content and also low sulfate content.

The carboxylic esters produced by the process of the invention can generally be used in all of the thermoplastically processible polymers produced with use of plasticizer. It is preferable that these thermoplastic polymers are selected from polyvinyl chloride (PVC), polyvinyl butyral (PVB), vinyl acetate homo- and copolymers, styrene homo- and copolymers, polyacrylates, thermoplastic polyurethanes (TPU), polysulfides, and mixtures thereof.

The carboxylic esters produced by the process of the invention can also be used in the production of elastomers. These are preferably natural rubber (NR) or rubbers produced synthetically, for example polyisoprene rubber (IR), styrene-butadiene rubber (SBR), butadiene rubber (BR), nitrile-butadiene rubber (NBR), or chloroprene rubber (CR).

The invention is explained in more detail with reference to the figures described below and to the inventive examples. The figures and inventive examples here are not to be interpreted as restricting the invention.

The examples and figures below use the following abbreviations:
MSA for methanesulfonic acid,
PTSA for para-toluenesulfonic acid,
MSTFA for N-methyl-N-(trimethylsilyl)trifluoroacetamide,
DOTP for bis(2-ethylhexyl) terephthalate (dioctyl terephthalate),
DINP for diisononyl phthalate,
TOTM for tris(2-ethylhexyl) trimellitate,
APHA for American Public Health Association,
OiPr for isopropanolate.

DESCRIPTION OF FIGURES

FIG. 1:

FIG. 1 shows the course of the MSA-catalyzed esterification reaction of terephthalic acid and 2-ethylhexanol (inventive example 1) by using the percentage proportions, determined by gas chromatography, of the reaction product DOTP, of the starting material 2-ethylhexanol, and also of the byproduct di(2-ethylhexyl) ether in the reaction mixture. The amount of water removed is also stated.

EXAMPLES

I) Analytical Studies

I.a Gas-Chromatographic Study:

For gas-chromatographic studies, an excess of MSTFA (N-methyl-N-(trimethylsilyl)trifluoroacetamide) was admixed with the samples, and the mixture was heated for 30 min to 100° C. so that all of the acidic protons had been converted to the appropriate trimethylsilyl groups. After cooling, the samples were diluted with N,N-dimethyl-formamide (DMF).

Data relating to the gas-chromatographic separation system and to the separation method:
Equipment: Agilent 6890 Series
Injector: split/splitless with split liner siltec-deactivated (Restec #20713-214.5)
Column: Optima 1 (length=25 m, internal diameter=0.25 mm, external diameter=0.40 mm, film thickness 0.25 μm) from Macherey & Nagel
Detector: FID with 300 ml/min of air, 30 ml/min of hydrogen and 30 ml/min of make-up gas (nitrogen)
Carrier gas: nitrogen
Flow rate: 0.7 ml/min at 8.3 psi (with oven temperature 80° C.)
Split: 1:36, split flow: 28 ml/min, septum purge 2.0 ml/min (with oven temperature 80° C.)
Injector temperature: 340° C.
Injection volume: 1 μl
Detector temperature: 320° C.

Temperature Program:
Start: 120° C.
Residence time 1: 0 min
Temperature gradient 1: 20° C./min
Final temperature 1: 350° C.
Residence time 2: 5 min
Total running time: 16.5 min When the samples comprise high boilers, residence time 2 can alternatively be set to 30 min. Total running time then increases to 41.5 min.

Evaluation: Empower-3 software using area %
Retention Times:

| | |
|---|---|
| DOTP (peak 1) | 10.456 min (main peak) |
| DOTP (peak 2) | 10.202 min (isomer of peak 1) |
| 2-Ethyl-1-hexanol-MSTFA | 2.87 min |
| 2-Ethyl-1-hexyl mesylate | 4.44 min |
| Terephthalic-acid-MSTFA | 6.39 min |
| Monoester-MSTFA | 8.52 min |
| Ethylhexanol-di-ether | 4.89 min |

I.b Determination of Acid Number:

Acid number, stated in mg KOH/g of sample, is determined in propanol by potentiometric titration with 0.1 mol/L of standard tetrabutylammonium hydroxide solution. Equipment and electrodes from Metrohm are used for the determination.

I.c Determination of APHA Hazen Color Value:

Hazen color value is measured by the method based on DIN/EN/ISO 6271-2 (March 2005) on undiluted material against water as reference. Round cells of diameter 11 mm are used. Equipment used can by way of example be a Dr. Lange LICO 400 photometer.

II) Production Examples

Inventive Example 1

Synthesis of DOTP from Terephthalic Acid and 2-Ethylhexanol with MSA as Catalyst Terephthalic acid (249 g, 1.50 mol), 2-ethylhexanol (469 g, 3.60 mol), and methanesulfonic acid (Lutropur MSA, BASF, 6.13 g of an approximately 70% by weight aqueous solution, 0.045 mol) are used as initial charge in a 1.6 L double-walled stirred-tank reactor which can be heated by way of a programmable thermostat and has anchor stirrer, Jennewein water separator, condenser, nitrogen inlet, and connection for a vacuum pump, and the reactor is inertized with nitrogen. The nitrogen flow rate through the apparatus was set to from 2 to 4 L h$^{-1}$, and the reaction mixture was heated to 180° C., whereupon an azeotropic mixture of water and 2-ethylhexanol was formed and liquefied in the condenser, and was passed through to the water separator. After phase separation, the organic phase was returned to the reactor, while the aqueous phase was discarded. The water removed was weighed and used to monitor the reaction. In order to ensure a constant flow of distillate and to achieve full conversion in the reaction, the temperature was increased within 4 h in stages to 200° C. and finally within a period of 2 h to 215° C. The temperature was kept at that level until the reaction mixture took the form of a clear solution and the calculated amount of water derived from the reaction and from the methanesulfonic acid used had been collected (56 g). The reaction time was 7.25 h. The reaction mixture was also studied by gas chromatography. After cooling to room temperature, the acid number of the mixture was determined by the known methods, and the mixture was rendered alkaline by using 150 mL of 1.2% NaOH (50% excess, based on the acid number determined). After the phases had been separated, the mixture was washed with water until neutral, and the excess 2-ethylhexanol, and also all of the other compounds with a boiling point below the boiling point of DOTP, were drawn off in vacuo (205° C., 8 mbar). The resultant product was filtered through a pressure-filter funnel. Reaction time: 7.25 h. Yield: 91%. GC content: 98.73% of DOTP (area %). Color value (APHA, Hazen): 12.

Inventive Example 2

Synthesis of DOTP from Terephthalic Acid and 2-Ethylhexanol with MSA as Catalyst Under Reduced Pressure The reaction was carried out as described in inventive example 1. However, the pressure during the reaction was reduced from 750 mbar to 400 mbar, and the temperature was kept at from 140 to 180° C. Reaction time: 8 h. Yield: 96%. GC content: 97.27% of DOTP (area %).

Inventive Example 3

Synthesis of Diisononyl Phthalate (DINP) from Phthalic Anhydride and Isononanol with MSA as Catalyst Phthalic anhydride (224 g, 1.50 mol), isononanol (Nonanol N, BASF SE) (519 g, 3.60 mol), and methanesulfonic acid (Lutropur MSA, BASF, 3.07 g of an approximately 70% by weight aqueous solution, 0.023 mol) are used as initial charge in a 1.6 L double-walled stirred-tank reactor which can be heated by way of a programmable thermostat and has anchor stirrer, Jennewein water separator, condenser, nitrogen inlet, and connection for a vacuum pump, and the reactor is inertized with nitrogen. The nitrogen flow rate through the apparatus was set to from 2 to 4 L h$^{-1}$, and the reaction mixture was heated to 170° C., whereupon an azeotropic mixture of water and isononanol was formed and liquefied in the condenser, and was passed through to the water separator. After phase separation, the organic phase was returned to the reactor, while the aqueous phase was discarded. The water removed was weighed and used to monitor the reaction. In order to ensure a constant flow of distillate and to achieve full conversion in the reaction, the temperature was increased within a period of 2 h in stages to 217° C. After 2.5 hours, the calculated amount of water had been removed, and the reaction mixture was cooled to room temperature. The acid number of the mixture was determined by the known methods, and the mixture was rendered alkaline by using 150 mL of 1.2% NaOH (50% excess, based on the acid number determined). After the phases had been separated, the mixture was washed with water until neutral, and the excess isononanol, and also all of the other compounds with a boiling point below the boiling point of DINP, were drawn off in vacuo (231° C., 8 mbar). The resultant product was filtered through a pressure-filter funnel. Reaction time: 2.5 h. Yield: 92.8%. GC content: 99.65% of DINP (area %). Color value (APHA, Hazen): 22. Acid number: 0.1 mg KOH/g.

Inventive Example 4

Synthesis of Tris(2-Ethylhexyl) Trimellitate (TOTM) from Trimellitic Anhydride and 2-Ethylhexanol with MSA as Catalyst Trimellitic anhydride (252.2 g, 1.31 mol), 2-ethylhexanol (564 g, 4.33 mol), and methanesulfonic acid (Lutropur MSA, BASF, 2.68 g of an approximately 70% by weight aqueous solution, 0.020 mol) are used as initial charge in a 1.6 L double-walled stirred-tank reactor which can be heated by way of a programmable thermostat and has anchor stirrer, Jennewein water separator, condenser, nitrogen inlet, and connection for a vacuum pump, and the reactor is inertized with nitrogen. The nitrogen flow rate through the apparatus was set to from 2 to 4 L h$^{-1}$, and the reaction mixture was heated to 180° C., whereupon an azeotropic mixture of water and 2-ethylhexanol was formed and liquefied in the condenser, and was passed through to the water separator. After phase separation, the organic phase was returned to the reactor, while the aqueous phase was discarded. The water removed was weighed and used to monitor the reaction. In order to ensure a constant flow of distillate and to achieve full conversion in the reaction, the temperature was increased within a period of 3 h in stages to 208° C. The temperature was then kept at that level until the calculated amount of water derived from the reaction and from the methanesulfonic acid used had been collected (49 g). The reaction time was 3 h. After cooling to room temperature, the acid number of the mixture was determined by the known methods, and the mixture was rendered alkaline by using 1.80 g of sodium hydrogencarbonate (50% excess, based on the acid number determined). The excess 2-ethylhexanol, and also all of the other compounds with a boiling point below the boiling point of TOTM, were drawn off in vacuo (197° C., 6 mbar). The resultant product was filtered through a pressure-filter funnel. Reaction time: 3 h. Yield: 93%. GC content: 97.40% of TOTM (area %). Color value (APHA, Hazen): 38.

Inventive Example 5

Synthesis of DOTP from Terephthalic Acid and 2-Ethylhexanol with PTSA as Catalyst DOTP was produced by the process described in inventive example 1. However, PTSA (8.56 g, 0.045 mol) (p-toluenesulfonic acid monohydrate from Sigma-Aldrich, ACS reagent grade, ≥98.5%, <0.3% of $SO_4^{2-}$) was used as catalyst instead of methanesulfonic acid. Reaction time: 8 h. Yield: 91%. GC content: 98.09% of DOTP (area %). Color value (APHA, Hazen): 24.

Comparative Example CE1

Synthesis of DOTP from Terephthalic Acid and 2-Ethylhexanol with MSA as Catalyst, without Nitrogen DOTP was produced by the process described in inventive example 1. However, passage of nitrogen through the mixture was omitted. Reaction time: 14 h. Yield: 91%. GC content: 99% of DOTP (area %). Color value (APHA, Hazen): 578.

Comparative Example CE2

Synthesis of DOTP from Terephthalic Acid and 2-Ethylhexanol with Sulfuric Acid as Catalyst DOTP was produced by the process described in inventive example 1. However, sulfuric acid (2.22 g, 0.023 mol) was used as catalyst instead of methanesulfonic acid. The temperature at the end of the reaction was 236° C. Reaction time: 8 h. Yield: 88%. GC content: 99.37% of DOTP (area %). The color value was too high to be recorded on the Hazen scale. Iodine color value: 8.6.

Comparative Example CE3

Synthesis of DOTP from Terephthalic Acid and 2-Ethylhexanol with Ti(OiPr)$_4$ as Catalyst DOTP was produced by the process described in inventive example 1. However, Ti(OiPr)$_4$ (2.22 g, 0.023 mol) was used as catalyst instead of methanesulfonic acid. The temperature at the end of the reaction was 233° C. Reaction time: 18 h. Yield: 82%. GC content: 97.70% of DOTP (area %). Color value (APHA, Hazen): 25.

Inventive Example 6

Synthesis of TOTM from Trimellitic Anhydride and 2-Ethylhexanol with PTSA as Catalyst TOTM was produced by the process described in inventive example 4. However, PTSA (3.88 g, 0.02 mol) (p-toluenesulfonic acid monohydrate from Sigma-Aldrich, ACS reagent grade, ≥98.5%, <0.3% of SO$_4^{2-}$) was used as catalyst instead of methanesulfonic acid. The temperature at the end of the reaction was 207° C. Reaction time: 4 h. Yield: 91%. GC content: 96.99% of TOTM (area %). Color value (APHA, Hazen): 104.

Comparative Example CE4

Synthesis of TOTM from Trimellitic Anhydride and 2-Ethylhexanol with Ti(OiPr)$_4$ as Catalyst TOTM was produced by the process described in inventive example 4. However, Ti(OiPr)$_4$ (1.11 g, 0.004 mol) was used as catalyst instead of methanesulfonic acid. The temperature at the end of the reaction was 217° C. Reaction time: 6 h. Yield: 90%. GC content: 96.93% of TOTM (area %). Color value (APHA, Hazen): 187.

Inventive Example 7

Synthesis of DINP from Phthalic Anhydride and Isononanol (Nonanol N, BASF SE) with PTSA as Catalyst (p-Toluenesulfonic Acid Monohydrate from Sigma-Aldrich, ACS Reagent Grade, ≥98.5%, <0.3% of SO$_4^{2-}$)

DINP was produced by the process described in inventive example 3 from 224 g (1.50 mol) of phthalic anhydride and 476 g of Nonanol N (3.30 mol). However, PTSA (4.37 g, 0.023 mol) was used as catalyst instead of methanesulfonic acid. The temperature at the end of the reaction was 217° C. Reaction time: 4 h. Yield: 94%. GC content: 99.32% of TOTM (area %). Color value (APHA, Hazen): 38.

Comparative Example CE5

Synthesis of DOTP from Terephthalic Acid and 2-Ethylhexanol with Use of MSA with High Total Chlorine Content and High Sulfate Content DOTP was produced as in inventive example 1. However, MSA with high total chlorine content and high sulfate content was used as catalyst. After work-up, the color value was 57 (APHA, Hazen), and no further characterization of the mixture was carried out.

Comparative Example CE6

Synthesis of DOTP from Terephthalic Acid and 2-Ethylhexanol with Use of PTSA with High Sulfate Content DOTP was produced as in inventive example 5. However, PTSA with high sulfate content was used as catalyst. After work-up, the color value was 44 (APHA, Hazen), and no further characterization of the mixture was carried out.

III) Comparative Examples Relating to the Discoloration of Esterification Products, Depending on the Quality of the Esterification Catalyst Used, Taking a Model System Based on Oleic Acid and without Introduction of any Inert Gas 1% by weight of acid (MSA and sulfuric acid) and, respectively, 2% by weight of PTSA (because of the approximately doubled molar mass of 190 g/mol versus 96 g/mol for MSA) were admixed with 80 g, weighed into 100 ml laboratory glass bottles, of an equimolar mixture of oleic acid and 2-ethylhexanol. The various bottles were positioned into a heated stirrer unit with capacity for 15 samples and stirred at 150° C. for a period of 24 h. A sample was then taken from each mixture and the Hazen color value was determined:

| Example | Catalyst | Sulfate content [%] | Hazen color value [APHA] |
|---|---|---|---|
| 1 | MSA (A), Lutropur ® MSA100 | <0.005% (<50 ppm) | 344 |
| 2 | MSA (B) | 0.02% (200 ppm) | 528 |
| 3 | PTSA (A), solid | 0.19% | 542 |
| 4 | PTSA (B), 65% strength solution | 0.32% | 866 |
| 5 | PTSA (C), solid | 10% | >1000 |
| 6 | Sulfuric acid | 96% | >1000 |

Color values achieved with the acid catalysts used with high sulfate content were found to be poor.

The invention claimed is:

1. A process for producing a carboxylic ester, the process comprising:
   reacting a reaction mixture comprising a carboxylic acid, a carboxylic anhydride, or both, and an alcohol R$^1$—OH, an alcohol R$^2$—[O—X]$_n$—OH, or both, in a reaction system comprising one or more reactors, in the presence of methanesulfonic acid wherein a sulfate content of the methanesulfonic acid is at most 50 ppm and a chlorine content of the methanesulfonic acid is at most 20 ppm, and at a reaction mixture temperature of from 150° C. to 240° C.;
   introducing an inert gas into the reaction system during the reacting;
   removing, from the one or more reactors, water formed during the reacting as an azeotropic mixture with the alcohol R$^1$—OH, the alcohol R$^2$—[O—X]$_n$—OH, or both; and returning at least some of the alcohol $R^1$—OH, the alcohol $R^2$—[O—X]$_n$—OH, or both, removed from the one or more reactors to the reaction system, to obtain a carboxylic ester, wherein:

$R^1$ represents an unbranched or branched $C_5$-$C_{13}$-alkyl group, or a $C_5$-$C_6$-cycloalkyl group that is optionally substituted by at least one $C_1$-$C_{10}$-alkyl moiety;

$R^2$ represents an unbranched $C_1$-$C_{13}$-alkyl group or a branched $C_3$-$C_{13}$-alkyl group;

X represents an unbranched $C_2$-$C_5$-alkylene group or branched $C_3$-$C_5$-alkylene group; and n has the value 1, 2 or 3.

2. The process according to claim 1, where the inert gas is passed into at least one of the reactors below a liquid surface of the reaction mixture, such that the inert gas bubbles through the reaction mixture.

3. The process of claim 1, wherein:

the reaction system comprises a cascade of at least two reactors; and the inert gas is introduced at least into a first reactor of the cascade.

4. The process of claim 1, wherein the reaction occurs continuously.

5. The process of claim 1, wherein the inert gas is nitrogen.

6. The process of claim 1, wherein $R^1$ is a n-octyl group, a 2-ethylhexyl group, a n-nonyl group, an isononyl group, an isodecyl group, a 2-propylheptyl group, a n-undecyl group or an isoundecyl group.

7. The process of claim 1, wherein the alcohol $R^1$—OH is 2-ethylhexanol.

8. The process of claim 1, wherein:

$R^2$ is an unbranched $C_1$-$C_9$-alkyl group or a branched $C_3$-$C_9$-alkyl group;

X is an unbranched $C_2$-$C_3$-alkylene group or a branched $C_3$-$C_4$-alkylene group; and n has the value 1 or 2.

9. The process of claim 1, wherein the alcohol $R^2$—[O—X]$_n$—OH is 2-butoxyethanol, 2-(2-butoxyethoxy)ethanol, 1-methoxy-2-propanol, 3-methoxypropanol, or a mixture thereof.

10. The process of claim 1, comprising reacting an alcohol $R^1$—OH, an alcohol $R^2$—[O—X]$_n$—OH, or both, with an aromatic mono-, di-, tri-, or tetracarboxylic acid or anhydride thereof, an aliphatic mono- or dicarboxylic acid or anhydride thereof, a hydroxycarboxylic acid or anhydride thereof, an alicyclic mono-, di-, tri-, or tetracarboxylic acid or anhydride thereof, a heterocyclic dicarboxylic acid or anhydride thereof, or a mixture thereof.

11. The process of claim 1, wherein the carboxylic acid, the carboxylic anhydride, or both, is selected from the group consisting of acetic acid, acetic anhydride, benzoic acid, benzoic anhydride, phthalic acid, phthalic anhydride, isophthalic acid, terephthalic acid, trimellitic acid, trimellitic anhydride, pyromellitic acid, pyromellitic dianhydride, and mixtures thereof.

12. The process of claim 1, wherein the carboxylic acid, the carboxylic anhydride, or both, is selected from the group consisting of acetic acid, acetic anhydride, benzoic acid, benzoic anhydride, terephthalic acid, trimellitic acid, trimellitic anhydride, and mixtures thereof.

13. The process of claim 1, comprising reacting terephthalic acid with 2-ethylhexanol to produce bis(2-ethylhexyl)-terephthalate.

14. The process of claim 1, comprising reacting 2-butoxyethanol, 2-(2-butoxyethoxy)ethanol, 1-methoxy-2-propanol, 3-methoxypropanol, or a mixture thereof, with acetic acid or acetic anhydride to produce 2-butoxyethyl acetate, 2-(2-butoxyethoxy) ethyl acetate, 1-methoxy-2-propyl acetate, 3-methoxypropyl acetate, or a mixture thereof.

15. The process of claim 1, wherein the alcohol $R^1$—OH, the alcohol $R^2$—[O—X]$_n$—OH, or both, is present in a 1.01- to 2.0-fold molar excess, based on carboxylic acid equivalents of the carboxylic acid, a carboxylic anhydride, or both.

16. The process of claim 1, wherein a sulfate content of the methanesulfonic acid is at most 20 ppm.

17. The process of claim 1, wherein a proportion of the catalyst is from 0.5 to 5 mol %, based on a molar amount of carboxylic acid groups reacted.

* * * * *